United States Patent [19]

Goulait

[11] Patent Number: 5,326,612
[45] Date of Patent: Jul. 5, 1994

[54] NONWOVEN FEMALE COMPONENT FOR REFASTENABLE FASTENING DEVICE AND METHOD OF MAKING THE SAME

[75] Inventor: David J. K. Goulait, Cincinnati, Ohio
[73] Assignee: The Procter & Gamble Company, Cincinnati, Ohio
[21] Appl. No.: 703,441
[22] Filed: May 20, 1991
[51] Int. Cl.$^5$ .................. A44B 17/00; B32B 3/06
[52] U.S. Cl. ................... 428/100; 24/450; 24/451; 24/452; 428/212; 428/219; 428/220; 428/284; 428/287; 428/296; 428/292; 428/303
[58] Field of Search ............... 428/100, 284, 287, 296, 428/292, 303, 212, 219, 220; 24/450, 451, 452

[56] References Cited

U.S. PATENT DOCUMENTS

| | | | |
|---|---|---|---|
| 2,039,312 | 5/1936 | Goldman | 154/46 |
| 2,496,820 | 2/1950 | Smith | 155/184 |
| 2,991,843 | 7/1961 | Bell, Jr. | 183/51 |
| 3,005,219 | 10/1961 | Miller | 15/98 |
| 3,094,330 | 6/1963 | Smith | 273/54 |
| 3,176,364 | 4/1965 | Dritz | 24/213 |
| 3,214,323 | 10/1965 | Russell et al. | 161/148 |
| 3,266,113 | 8/1966 | Flanagan, Jr. | 24/204 |
| 3,266,841 | 8/1966 | Altman | 297/220 |
| 3,277,547 | 10/1966 | Billarant | 24/204 |
| 3,302,232 | 2/1967 | Wasiloff et al. | 15/230.17 |
| 3,319,307 | 5/1967 | Mariforio | 24/204 |
| 3,327,708 | 6/1967 | Sokolowski | 128/156 |
| 3,405,430 | 10/1968 | Sidelman | 24/204 |
| 3,469,289 | 2/1969 | Whitacre | 24/205.17 |
| 3,490,107 | 1/1970 | Brumlik | 24/204 |
| 3,494,006 | 1/1970 | Brumlik | 24/204 |
| 3,665,921 | 5/1972 | Stumpf | 128/287 |
| 3,665,922 | 5/1972 | Skora | 128/298 |
| 3,694,867 | 10/1972 | Stumpf | 24/204 |
| 3,708,833 | 1/1973 | Ribich et al. | 24/204 |
| 3,895,797 | 7/1975 | Moore | 24/450 |
| 3,905,071 | 9/1975 | Brumlik | 24/204 |
| 3,949,128 | 4/1976 | Ostermeier | 428/152 |
| 4,082,886 | 4/1978 | Butterworth et al. | 428/284 |
| 4,162,344 | 7/1979 | Rones | 428/212 |
| 4,355,066 | 10/1982 | Newman | 428/198 |
| 4,374,888 | 2/1983 | Bornslaeger | 428/198 |
| 4,379,192 | 4/1983 | Wahlquist et al. | 428/156 |
| 4,600,618 | 7/1986 | Raychok | 428/100 |
| 4,725,473 | 2/1988 | Van Gompel et al. | 428/156 |
| 4,737,404 | 4/1988 | Jackson | 428/284 |
| 4,761,318 | 8/1988 | Ott et al. | 428/85 |
| 4,761,322 | 8/1988 | Raley | 428/198 |
| 4,959,265 | 9/1990 | Wood et al. | 428/343 |
| 4,973,326 | 11/1990 | Wood et al. | 604/391 |

OTHER PUBLICATIONS

U.S. patent application Ser. No. 07/355,065 filed by Noel, et al. on May 17, 1989.
U.S. patent application Ser. No. 07/632,283 filed by Thomas, et al. on Dec. 21, 1990.
U.S. patent application Ser. No. (not assigned yet) filed the same day as the present application by David J. K. Goulait, discloses a multi-layer female component for a refastenable fastening device and method of making the same. (Ser. No. 07/382,516–Jul. 19, 1989.)

Primary Examiner—Ellis P. Robinson
Assistant Examiner—Nasser Ahmad
Attorney, Agent, or Firm—Steven W. Miller; Jeffrey V. Bamber; E. Kelly Linman

[57] ABSTRACT

A female component is provided for engaging a complementary hook component in a refastenable fastening device. The female component comprises a nonwoven web secured to a backing. The nonwoven web has characteristics that are specifically suited for entangling and holding the hooks of the mating hook component. The nonwoven web has a basis weight of between about 6 and about 42 grams/meter$^2$. The nonwoven web may comprise, among other types of nonwovens, a carded web with fibers between about 2.5 cm. and about 13 cm. long, or a spunbonded web with continuous length fibers. The denier of the fibers should be between about 0.5 and about 15. The total area occupied by any bonds between the fibers comprising the nonwoven web is less than about six percent of the total area of the web. The nonwoven web is secured to the backing, preferably autogeneously. The total area occupied by both the bonds between the fibers comprising the nonwoven web and by the bonds between the nonwoven web and the backing is between about 10 percent and about 35 percent of the total area of the female component. A fastening device having a hook fastening component and a female component that comprises the nonwoven female component of the present invention is also provided. The fastening device can be used on disposable articles, such as disposable diapers.

47 Claims, 6 Drawing Sheets

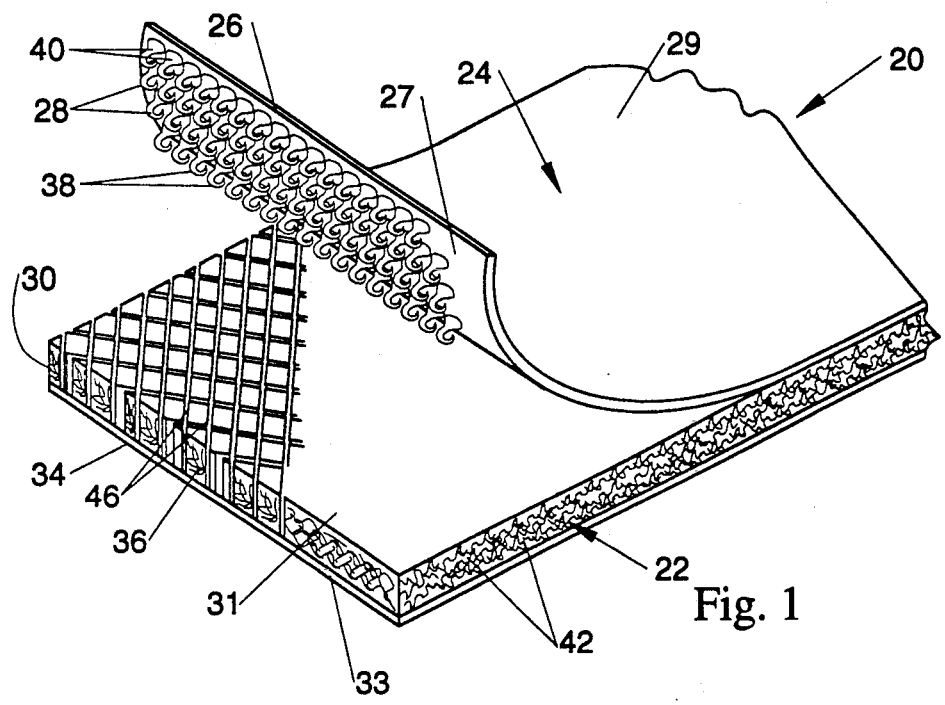
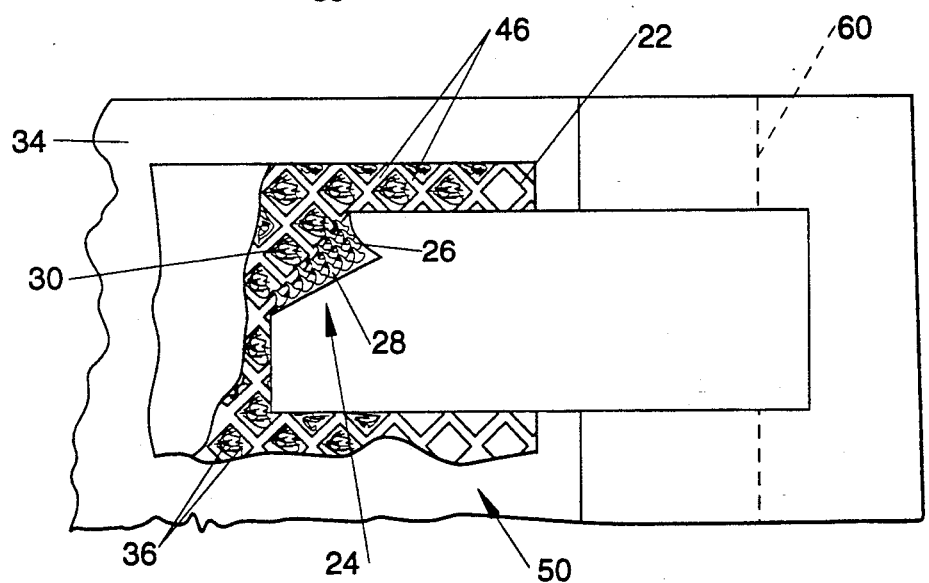
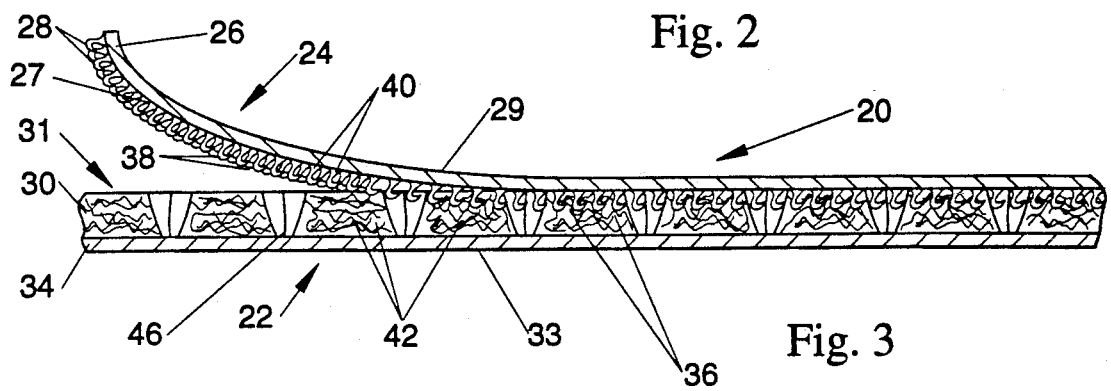

NONWOVEN FEMALE COMPONENT FOR REFASTENABLE FASTENING DEVICE AND METHOD OF MAKING THE SAME

FIELD OF THE INVENTION

The present invention relates to a female component for a mechanical refastenable fastening device. More particularly, this invention relates to a low-cost nonwoven female component for such a fastening device, and a method for producing such a component.

BACKGROUND OF THE INVENTION

Refastenable fastening devices of the hook and loop-type are currently used widely in a great number of situations. Such refastenable fastening devices have been used in clothing, disposable articles, and various miscellaneous articles such as safety belts and the like. Such devices are used when it is desirable to create a refastenable bond between two or more articles or between several surfaces of the same article. In certain applications, these refastenable fastening devices have replaced conventional buckles, zippers, buttons, snaps, tie fasteners, and sewing.

A popular type of mechanical fastener currently in wide use which utilizes mechanical entanglement to create a refastenable bond is sold under the trademark "VELCRO". VELCRO fastening devices are described in greater detail in U.S. Pat. No. 2,717,437, U.S. Pat. No. 3,009,235, U.S. Pat. No. 3,266,113, U.S. Pat. No. 3,550,837, U.S. Pat. No. 4,169,303, and U.S. Pat. No. 4,984,339.

VELCRO fasteners utilize two components, a male component and a female component. The male and female components are often referred to as the hook and loop components, respectively. The hook component consists of a fabric which contains a plurality of resilient, upstanding hook-shaped elements. The female component of the fastening device consists of a fabric containing a plurality of upstanding loops on its surface. When the hook component and the loop component are pressed together in a face-to-face relationship to close the fastening device, the hooks entangle the loops forming a plurality of mechanical bonds between the individual hooks and loops. When these bonds have been created, the components will not generally disengage under normal conditions. This is because it is very difficult to separate the components by attempting to disengage all of the hooks at once. However, when a gradual peeling force is applied to the components, disengagement can be easily effected. Under a peeling force, since the hooks are comprised of a resilient material, they will readily open to release the loops.

This type of fastening device has been found especially useful on disposable articles such as disposable garments, disposable diapers, disposable packages, cartons and the like. Such fastening devices provide a secure closing means. However, the use of existing fastening devices of this type on disposable articles has been limited due to the fact that such fastening devices are relatively costly. The major reason that such fastening devices are costly is that they have high manufacturing costs. These high manufacturing costs are associated with both the hook and loop components of these devices.

Conventional hook and loop components are typically formed by making a fabric with a number of woven loops extending outwardly from a backing. The loops may be provided by weaving a base fabric containing supplementary threads to form the loops, or by knitting loops into a fabric. In other hook and loop components, the loops may be formed by pleating or corrugating processes. The hook components of such fastening devices are typically formed by subsequently cutting the loops. The cut loops serve as the hooks of the hook component.

These processes generally produce costly hook and loop fastening materials because they are relatively slow. The hook and loop components of such fastening devices are also usually made out of the same relatively expensive material. This material is generally relatively expensive because the material used in the hook component needs to be resilient so that the hooks can disengage from the loop component when the device is opened.

Several attempts have been made to make alternative types of female components for fastening devices. However, such attempts have generally suffered from a number of drawbacks.

U.S. Pat. No. 3,694,867 issued to Stumpf on Oct. 3, 1972 discloses a "separable clasp" having a female component that comprises a "high loft" nonwoven fabric and a backing layer of consolidated flexible adhesive. U.S. Pat. No. 4,761,318 issued to Ott, et al. on Aug. 2, 1988 discloses a loop fastener that can contemporaneously be both formed and also attached to a substrate without the need for any additional steps such as sewing or utilizing pressure sensitive adhesives to affix it to the substrate. The female components disclosed in these patents suffer from the drawback that they are still made by processes that involve mechanically manipulating fibers in the form of loops. Thus, the female components described therein do not appear to significantly less expensive to manufacture than conventional loop components.

U.S. Pat. No. 3,708,833 issued to Ribich, et al. on Jan. 9, 1973 discloses a refastenable fastening device having a female component that comprises reticulated urethane foam secured to a backing layer. The female component disclosed in the Ribich, et al. patent suffers from the drawback that foams typically do not have enough openings for the hooks of conventional hook components to penetrate. In addition, reticulated foam usually does not have sufficient strength to hold such hooks when forces are applied to the fastening device. Further, manufacturing reticulated foam is a relatively expensive process.

U.S. Pat. No. 3,905,071 issued to Brumlik on Sep. 16, 1975 discloses a "press-through self-gripping device". The device disclosed in the Brumlik patent does not appear to be suitable for use in a refastenable fastening device that utilizes a conventional mating hook component with resilient hooks. The device disclosed in the Brumlik patent is intended to be used for fastening one or more sheets of material between a gripping member and a receiving member. The gripping member disclosed in the Brumlik patent has rigid and stiff needle-shaped elements for gripping elements. These needle-like elements are particularly unsuitable for use in fastening devices on disposable absorbent articles. The disclosure of the Brumlik patent, thus, appears to be limited to devices that employ gripping elements adapted to penetrate and pass through several sheets of material and lodge inside a receiving member.

Therefore, there is a need for a low-cost fastening device for disposable articles. In particular, there is a need for such low-cost fastening devices to perform in a manner comparable to the more expensive commercially-available fastening devices.

It is an object of the present invention to provide an improved low-cost female component for a fastening device.

It is another object of the present invention to form a low-cost female component for a refastenable fastening device without manipulating fibers in the form of loops.

It is another object of the present invention to provide a female component for a fastening device that can be used with both commercially-available hook components having resilient individual hooks, as well as less expensive hook components with more brittle hooks than those currently in use.

It is a further object of the present invention to provide a low-cost and improved method for producing such a female component.

These and other objects of the present invention will be more readily apparent when considered in reference to the following description and when taken in connection with the accompanying drawings.

SUMMARY OF THE INVENTION

The present invention provides a female component for engaging a complementary hook component in a refastenable fastening device. The female component of the present invention is capable of engaging a hook component which has a base with individual hook elements having blunt heads extending outward from the base. The female component does not require individual loops of the conventional type to be present. Typically, the hooks will be engaged by elements that present the female component with a relatively flat outwardly-facing surface.

The female component of the present invention comprises at least one nonwoven web secured to a backing. The nonwoven web serves to admit and entangle at least some of the hooks of a complementary hook component and to provide space for the hooks to occupy after they have been admitted. The backing is adjacent the nonwoven web and provides a foundation for the nonwoven web. The nonwoven web has a basis weight of between about 5-35 g/yd.$^2$ (between about 6 and about 42 grams/meter$^2$). The nonwoven web may comprise, among other types of nonwovens, a carded web with fibers between about 2.5 cm. and about 13 cm. long, or a spunbonded web with continuous length fibers. The fibers that comprise the nonwoven web have a denier of between about 0.5 and 15. The total plan view area occupied by any bonds between the fibers comprising the nonwoven web (the "inter-fiber bonds") is less than about 10 percent, more preferably less than about 6 percent, and most preferably, less than about 2½ percent of the total area of the web. The nonwoven web is secured to the backing, preferably, autogenously. The total plan view bonded area is the projected plan view area occupied by both any inter-fiber bonds of the nonwoven web and by the bonds between the nonwoven web and the backing. The total plan view bonded area is less than about 35 percent, preferably between about 10 percent and about 35 percent, more preferably between about 10 percent and about 18 percent of the total area of the nonwoven web.

The female component of the present invention is formed by a method comprising the steps of:

(a) providing a first material having a basis weight of between about 6 to about 42 g/meter$^2$ and being comprised of a plurality of fibers, wherein the plan view area occupied by any bonds between the fibers is less than about ten percent of the total area of the first material;

(b) providing a backing material; and (c) securing the first material and the backing material together to form a female component so that the total area occupied by both any bonds between the fibers comprising the first material and by the bonds between the first material and the backing is between about 10 percent and about 35 percent of the total area of the female component.

The female component described above can, thus, be made less expensively than conventional loop components because there is no need to mechanically manipulate fibers in the form of individual loops.

The present invention also relates to a fastening device having a hook fastening component and a female component comprising the nonwoven female component of the present invention. The hook fastening component comprises any of the well known hook fastening components as are known in the art which have a base and a number of individual hooks extending from the base. The hook component used can also comprise a less expensive hook component with more brittle hooks than those currently in use. The female component and the complementary hook fastening component provide a secure closing means that will resist shear stress and peel forces encountered during use.

The present invention also relates to disposable articles and more particularly to a disposable diaper having such an improved fastening device.

BRIEF DESCRIPTION OF THE DRAWINGS

While the specification concludes with claims particularly pointing out and distinctly claiming the subject matter which is regarded as forming the present invention, it is believed that the invention will be better understood from the following description in conjunction with the accompanying drawings in which:

FIG. 1 is a perspective view of the refastenable fastening device of the present invention.

FIG. 2 is a partially cut-away plan view of the female component of the present invention shown in use with a tape fastening system of a disposable diaper (only a portion of which is shown).

FIG. 3 is a side view of the fastening device shown in FIG. 1.

(FIG. 4 also shows the bonding between the nonwoven material and the backing in a slightly less schematic form).

DETAILED DESCRIPTION OF THE INVENTION

The Refastenable Fastening Device

Figure 4:
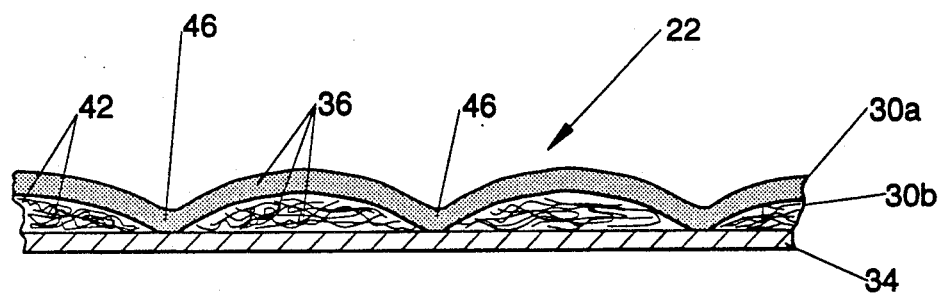
FIG. 4 is a side view of an alternative embodiment of the female component having a "skin friendly" layer of fibers forming its first surface.

1. Overall Characteristics of the Refastenable Fastening Device

A preferred embodiment of the refastenable fastening device of the present invention, fastening device 20, is shown in FIG. 1.

The fastening device 20 comprises the nonwoven female component 22 of the present invention and a complementary hook fastening component 24.

The male portion of the device, hook fastening component (or simply "hook component") 24, comprises a base, such as fabric 26. The fabric 26 has a first surface 27 and a second surface 29. The fabric 26 contains a plurality of upstanding engaging elements or "hooks" 28 extending from the first surface 27. The hooks 28 have heads 38. The heads 38 are on top of the shanks or stems 40 that extend from the first surface 27.

The female portion of the device, nonwoven female component (or simply "female component") 22, receives and engages the hooks 28 of the hook component 24. The female component 22 shown in FIG. 1 has a first, outwardly-facing surface 31 and a second, inwardly-facing surface 33. The female component 22 comprises at least one nonwoven web 30 secured to a backing 34. The nonwoven web 30 contains a plurality of structural components or structural elements. These structural elements comprise fibrous elements (or simply "fibers") 36. The fibers 36 entangle the hooks 28 of the hook component 24.

The arrangement of the parts of the female component 22 is shown in FIG. 1. The nonwoven web 30 is positioned on top of the backing 34. The nonwoven web 30 faces outward to form the first surface 31 of the female component 22. The nonwoven web 30 is exposed so that it will be available to entangle the hooks 28 of the hook component 24. The backing 34 is inwardly-oriented so it will be adjacent and generally joined to the portion of the article to which the female component 22 is attached.

The fastening device 20 of the present invention functions in the following manner. The fastening device 20 is closed when the female component 22 and the hook component 24 are pressed face-to-face against each other. When this happens, the hooks 28 are entangled by the fibers 36 of the nonwoven web 30. The nonwoven web 30 provides space for the hooks, particularly, the heads 38 of the hooks 28 to occupy when the fastening device 20 is closed. The backing 34 provides a supporting foundation for the nonwoven web 30. With the hooks 28 mechanically entangled by or "hooked" onto the fibers 36 (shown in the portion of the fastening device 20 to the right side in FIG. 1), the connection between the components resists the forces that may be exerted on the fastening device 20.

The fastening device 20 is opened by peeling the hook component 24 away from the female component 22 (or by peeling the female component 22 away from the hook component 24). If the hook component 24 has resilient hooks, the peeling action may cause the hooks 28 to be bent so that they are disengaged from mechanical entanglement with the fibers 36 of the nonwoven web 30. In other cases (particularly if the hooks 28 are relatively inflexible), the hooks 28 may be separated by breaking the fibers 36 of the female component 22. In either case, the hooks 28 are disengaged, and the hook component 24 is completely detached from the female component 22. The fastening device 20 is then capable of being refastened in the manner described above.

The components of the refastenable fastening device 20 are discussed more fully in the following sections of this description. The nonwoven female component 22 of the present invention is discussed in Section 2 below. The hook component 24 is discussed in Section 3. Section 4 gives examples of uses of the refastenable fastening device 20.

2. The Nonwoven Female Component

The nonwoven female component 22 shown in FIGS. 1–3 is one preferred embodiment of the female component of the refastenable fastening device 20 of the present invention. Several alternative embodiments are shown in the figures that follow FIGS. 1–3. It should be understood that the female component 22 is generally shown in schematic form for simplicity in most of the figures. The configuration of the female component 22 and the bonding of the nonwoven web 30 to the backing 34 more closely resembles that shown in FIG. 4 in the actual product.

The definitions of several terms are first provided to assist the reader in understanding the present invention.

The term "nonwoven female component", as used herein, is intended to be a shorthand way of referring to a female component for a fastening device that comprises a nonwoven web secured to a backing. It is not intended to limit the present invention to female components that are comprised entirely of nonwoven materials. Thus, the backing 34 may not be, and in many cases is not a nonwoven web.

The terms "web" and "layer", as used herein, may refer to several sheets or webs of the types of material described below. Thus, those terms are not limited to structures in the form of single layers or sheets of material.

The term "loop component", as used herein, refers to the portion of a hook and loop-type fastening device that is designed to engage the hooks of a complementary hook component. The nonwoven female component 22 of the present invention could be thought of as a replacement for a loop component. Generally, however, the nonwoven female component 22 does not require that loops of material be specifically formed to engage the hooks of a mating hook component. Typically, the individual fibers 36 of the nonwoven web 30 will serve to entangle the hooks 28, even though these fibers are not necessarily "looped".

The nonwoven female component 22 of the present invention should have certain characteristics.

The nonwoven female component 22 has characteristics that are specifically suited to receive the hooks 28 of a mating hook component 24. The fibers 36 of the nonwoven web 30 serve to entangle the individual hooks 28 of the mating hook component 24. The female component 22 uses at least one layer of lofted nonwoven material to both entangle and store the hooks 28 of the hook component 24. The female component 22 does not require the formation of loops of material extending outward from a backing. (Thus, for the purposes of the present invention, the female component 22 may be considered to be "loop-less".)

The term "loop", as used herein, refers to a fibrous material that is curved or doubled to form a closed curve into which a hook may be inserted. The term "loop", as used herein, also includes materials made by any process in which fibrous materials are manipulated, individually or collectively, to form loops, regardless of whether the fibers are formed into a closed or partially open curve. For the purposes of the present invention, however, the term "loop" does not include the fibers of nonwoven webs that are disposed within a web which are not separately manipulated.

The female component 22 has an outwardly-facing surface 31 that is relatively level, planar, or flat in comparison to the surfaces of conventional loop components which have many loops of material extending outward from a backing. The term "planar", as used herein, includes, but is not limited to those surfaces that lie in a single, relatively flat plane as shown in FIGS. 1-3, as well as those surfaces that are gradually curved such as shown in FIG. 4. The individual fibers 36 of the nonwoven web 30 may lie relatively flat at the surface 31 of the nonwoven web, and not be "looped". Although it is possible that they could be looped or lofted. However, such embodiments are less preferred.

The female component 22 should have sufficient space between the fibers 36 of the nonwoven web 30. The space should be sufficient to allow the hooks 28 to readily enter between the spaces (or interstices) between the fibers 36 of nonwoven web 30 when the hook component 24 is placed into a face-to-face relationship with the female component 22. The hooks 28 should be able to enter without piercing through these fibers 36. The hooks 28 should be able to enter, and if necessary, spread these fibers 36 apart. This should, however, require the application of relatively little, if any force (e.g., in comparison to that needed when using a "press-through" device such as that described in the Brumlik patent discussed above).

When the female component 22 is provided with such space between the fibers 36 of the nonwoven web 30, it will work with conventional, commercially available hook materials. The female component 22, however, is not limited to use with conventional hook materials having flexible, resilient hooks. It can also be used with hook materials that have less expensive, more brittle hooks. The female component 22 is also particularly well-suited for use with hook components having hooks with generally rounded and/or blunt heads. It does not require specially-made rigid, sharp hooks to be used. It is, however, possible for sharp hooks to be used with the female component 22.

Thus, when the female component 22 of the present invention is said to be "capable" of engaging a hook component with a certain type of hooks, this means that the type of hook component referred to can be used. The female component 22, however, is typically not limited to use with such a hook component; other types of hook components can usually also be used with the female component.

Figure 5:
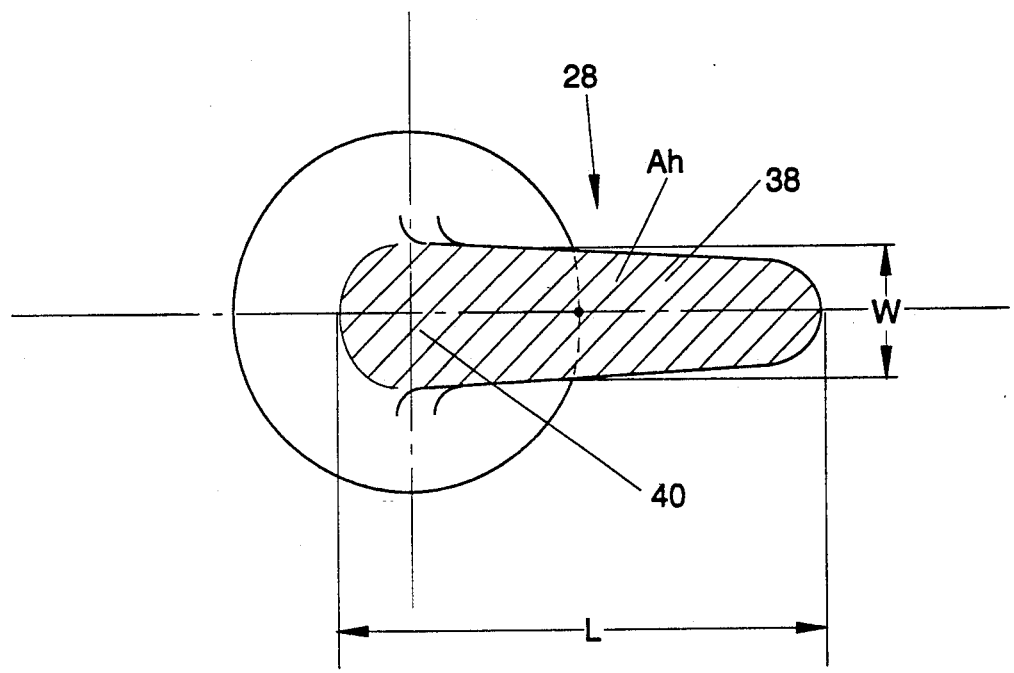
FIG. 5 is a plan view of an individual hook of the hook component.
Figure 6:
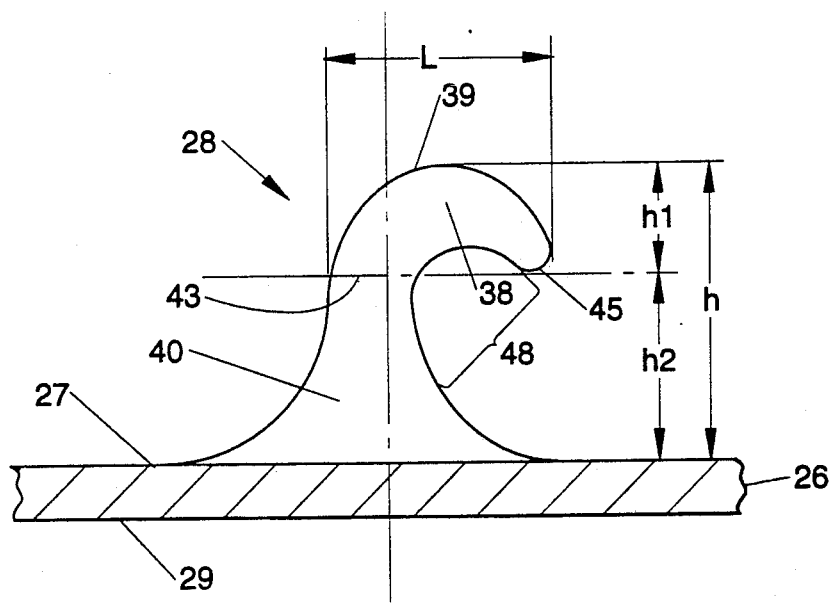
FIG. 6 is a side view of the hook shown in FIG. 5.

The amount of open space between the fibers 36 of the nonwoven web 30 required for the fastening device 20 to be operable is related to the size of the hooks 28 of the hook component 24. The dimensions of various parts of a hook 28 of one type are shown in FIGS. 5 and 6. The hook 28 shown in FIGS. 5 and 6 has an overall height h, and a head 38 with a certain length, width, and height, designated 1, w, and $h_l$, respectively.

The "head" of the hooks, as that term is used herein, refers the portions of the hook 28 that project laterally (or radially) outward from the stems 40 in one or more directions. Often, there will not be a line of demarcation between where the stem 40 of the hook 28 ends and where the head 38 begins. For the purposes of the present invention, the head 38 of the hooks 28 will be considered to begin at the portion of the stem 40 designated 43 in FIG. 6. This is the portion of the stem 40 that is spaced the same perpendicular distance away from the backing 36 as the lowermost point 45 on the head 38 of the hook 28. The lowermost point 45 is the portion of the head 38 spaced the smallest perpendicular distance, $h_2$, from the base 26 of the hook component 24.

The length 1 and width w of the hook's head 38 are most important in determining the amount of open space required between the fibers 36 of the nonwoven web 30. More specifically, the amount of open space between the fibers 36 of the nonwoven web 30 needed is generally determined by the dimensions known as the projected plan view area (or the "projected plan view dimensions") of the heads 38 of the hooks 28. This area is represented by reference letter $A_h$ in FIG. 5. This is the surface of the hooks 28 that will initially come in contact with the female component 22 of the present invention. Thus, the open space provided by between the fibers 36 of the nonwoven web 30 should be either slightly larger in dimensions than the projected plan view dimensions of the heads 38 of the hooks 28, or these fibers 36 should readily spread apart to such dimensions. Therefore, when large hooks 28 are used (that is, hooks having a relatively large $A_h$), there should be more open space than if relatively small hooks 28 are used.

The nonwoven web 30 is one basic element of the female component 22 of the present invention. The nonwoven web 30 is the portion of the female component 22 that admits and entangles at least some of the hooks 28 of the complementary hook component 24 and receives and provides space for these hooks 28 to occupy after they have been admitted.

The nonwoven web 30 used in the female component 22 may be any suitable nonwoven material. The term "nonwoven", as used herein, refers to fabrics made of fibers held together by interlocking or bonding which are not woven, knitted, felted, or the like. The, nonwoven web referred to herein may be a structure that is comprised of fibers that are initially substantially unbonded which are subsequently bonded to the backing 34. The nonwoven web referred to herein also includes webs of fibers that have some degree of inter-fiber bonding before such webs are bonded to the backing 34.

The nonwoven web 30 should have the open space described above. The amount of open space should be sufficient to allow a plurality of the hooks 28 of the mating hook component 24 to penetrate the thickness of the nonwoven web 30 when a hook component 24 is placed in face-to-face relationship with the female component 22. It is not necessary, however, that all of the hooks 28 of the hook component 24 penetrate the nonwoven web 30. The total number and distribution of such open spaces per unit area of the female component 22 should be adequate to accommodate a sufficient number of hooks 28 of the mating hook component 24 for the fastening device 20 to be operable.

The nonwoven web 30 should, therefore, be some type of structure that has sufficient space between its fibers 36 to readily admit the hooks 28 of the mating hook component 24. The nonwoven web 30 may alternatively, or additionally, be a structure that has fibers 36 that are arranged into a form that is flexible enough that the fibers 36 will move out of the way of the hooks 28 of the mating hook component 24 when the hook component 24 is placed in a face-to-face relationship with the female component 22 of the present invention.

When the fastening device 20 is closed, the hooks 28 of the mating hook component 24 first pass through the first surface 31 of the nonwoven web 30 and into the interior of the nonwoven web 30. The hooks 28 may initially penetrate the nonwoven web 30 to a greater depth than they will eventually be located when they have engaged the fibers 36 of the nonwoven web 30. In other words, there is usually an inward (toward the backing 34), then outward movement of the hooks 28 before they hook onto the fibers 36 of the nonwoven web 30.

The nonwoven web 30 should also be able to entangle and hold a sufficient number of the hooks 28 of the mating hook component 24 for the fastening device 20 to be operable. Therefore, the number of fibers 36 that comprise the nonwoven web 30 must be sufficient to entangle the hooks 28 so that the hooks will be held until a peeling force is applied to open the fastening device 20. These fibers must also have sufficient strength to hold the hooks 28 when forces that are not intended to open the fastening device 20 are applied.

The characteristics used in the nonwoven fabric industry, such as basis weight, length and denier of fibers are used to specify those nonwoven materials which have the qualities set forth above. The open area between the fibers 36 and the number of fibers (at least on a relative basis), can be approximated from the basis weight of the web. (For instance, a nonwoven web of a lesser basis weight will generally have greater open area and fewer fibers than a web of greater basis weight having the same denier and length fibers.) The strength of the web for use in a female component (at least on a relative basis) can be approximated from the basis weight of the web and the denier and material composition of the fibers.

Preferably, the nonwoven web used in the female component 22 of the present invention should have a relatively low basis weight so that there will be adequate space between the fibers 36 of the nonwoven web 30 for the hooks 28 of the mating hook component 24 penetrate the nonwoven web 30. Suitable nonwoven webs include those having a basis weight of between about 5 to about 35 g/yd$^2$ (about 6 to about 42 g/meter$^2$), more preferably, between about 15 to about 20 g/yd$^2$ (about 18 to about 24 g/meter$^2$). The basis weight is measured by die-cutting a certain size sample and weighing the sample on a standard scale. The weight and area of the sample determines the basis weight of the sample. The density of the sample, if needed, can be calculated from the basis weight of the sample and its caliper.

The caliper of the nonwoven web 30 should be sufficient for the heads 38 of the hooks 28 to catch onto the fibers 36 of the nonwoven web 30. The nonwoven web 30 is typically relatively thicker (that is, it has a greater caliper or is more "lofted") than the backing 34. This is because it must provide sufficient space to store the heads 38, and in many cases, at least a portion of the stems 40 of the hooks 28. The nonwoven web 30 may, therefore, be referred to as a "high loft" material.

The caliper of the nonwoven web 30 required depends on the height of the hooks 28 of the mating hook component 24. More particularly, the caliper depends on the dimension designated $h_1$ in FIG. 6, which represents the height of the heads 38 of the hooks 28. The caliper of the nonwoven web 30 should be at least as large as the height $h_1$ of the heads 38 of the hooks 28. This will assure that there is room to accommodate the inward and outward movement needed for the hooks 28 to hook onto the fibers 36 of the nonwoven web 30.

The caliper of the nonwoven web 30 can range to as large as the total height h of the hooks 28, or more. Thus, there is no fixed upper limit on the caliper of the nonwoven web 30. In some embodiments, the caliper of the nonwoven web 30 may be set so that the total caliper of the nonwoven web 30 is about the same as the height h of the hooks 28 to assure a good fit between the female component 22 and the hooks 28 of the mating hook component 24. The caliper should, however, preferably only be slightly larger than the height $h_1$ of the heads 38 of the hooks 28 of the mating hook component 24. If the caliper of the nonwoven web 30 is any greater, much of the additional material used to create such additional caliper will not be used, and will in effect, be wasted.

The caliper of the nonwoven web 30 may more specifically, by way of example, be sufficient to accommodate hooks of the sizes that are discussed in greater detail in Section 3 below. For instance, if the hooks 28 are between about 0.015 inch and about 0.025 inch (about 0.38 mm. to about 0.64 mm.) in overall height h and have heads 38 which are about 0.3 mm. in height, the caliper of the nonwoven web 30 should generally range from between slightly greater than about 0.3 mm. to about 0.38 mm, or to about 0.64 mm, respectively. In still other embodiments, the caliper of the nonwoven web 30 can be more or less depending on the size of the hooks 28 of the mating hook component 24. For example, the caliper of the nonwoven web 30 can be as small as about ½ or ¼ of the calipers set forth above, or less, if proportionately smaller hooks 28 are used.

The nonwoven web 30 is preferably comprised of relatively long fibers 36. The longer the fibers 36, the easier it is to bond these fibers 36 to each other and to the backing 34. If extremely short fibers are used, there may be an excessive number of unbonded loose fibers or partially bonded fibers (e.g., fibers with only one of their ends bonded). Such fibers will be uncapable of entangling and holding the hooks 28 of the hook component 24.

The lengths of the fibers 36 in the nonwoven web 30 depend upon the type of process used to make the nonwoven web 30. For instance, if a carded nonwoven web is used, the fibers that comprise such a web can have lengths that can range from about 0.5 inch to about 5 inches (from about 1 cm. to about 13 cm.). Preferably, the fibers are between about 2 inches and about 3 inches (between about 5 cm. and about 8 cm.) long. If, on the other hand, a spunbonded nonwoven web is used, the fibers or filaments of such a web will typically be continuous length.

The diameter of the fibers 36 is one factor that determines the strength of the nonwoven web 30. Generally, the larger the diameter of the fiber is, the stronger the fiber. The maximum diameter that can be used depends in part on the size of the gaps 48 of the hooks 28. The term "gap", as used herein, refers to the openings formed by the heads 38 of the hooks (the portions that grab the fibers 36). The diameter of the fibers 36 must not be so great that the heads 38 of the hooks 28 are unable to fit around and entangle the fibers 36. Typically, for currently-available hook components, the fibers 36 of the nonwoven web 30 should have a denier of between about 2 and about 15, more preferably, between about 3 and about 9, most preferably, between about 3 and about 6. If hook components become available that have hooks 28 that are substantially smaller than those currently available, the denier of the fibers could be between about 0.5 and about 15, or less. It is possible that fibers having deniers as low as between about 0.5 and about 1.0, or less, could be used. Such fibers may be referred to as "micro denier" fibers. (Denier is a unit of fineness of a yarn weighing one gram for each 9,000 meters, thus a 100 denier yarn is finer than a 150 denier yarn.)

The orientation of the individual fibers 36 in the nonwoven web 30 is also important. The orientation of the fibers 36 in a preferred nonwoven web 30 is preferably primarily in a single direction.

Figure 7:
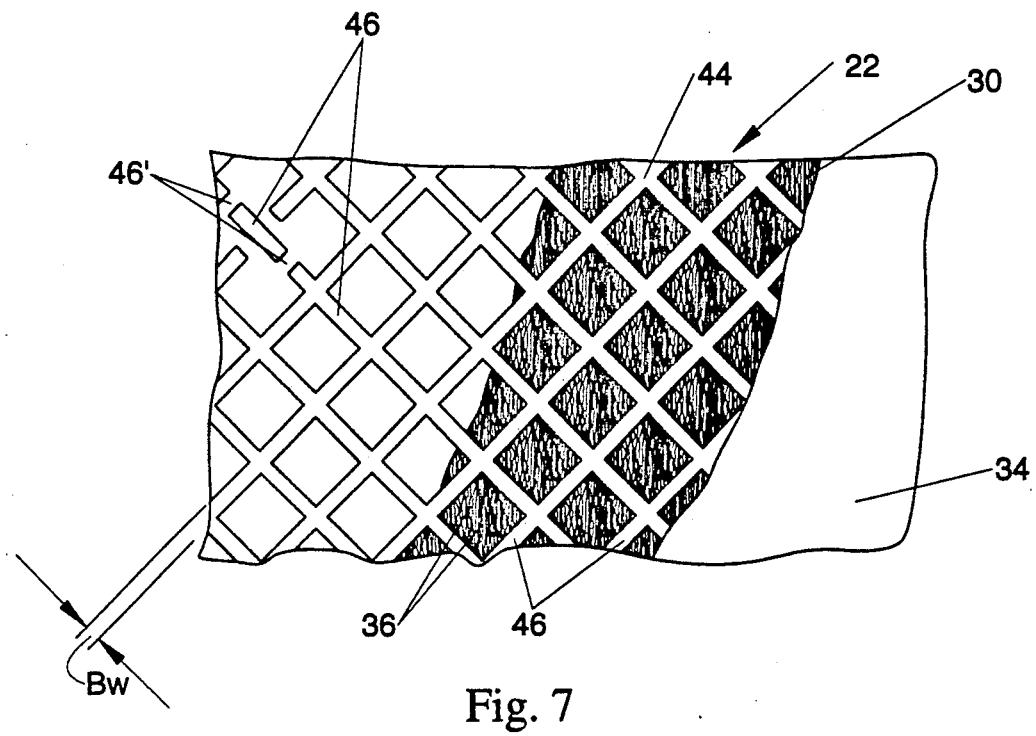
FIG. 7 is a plan view of an alternative embodiment of the nonwoven female component of the present invention which shows a preferred arrangement of fibers in the nonwoven web.

In addition, when the female component 22 is incorporated into the refastenable fastening device 20 of a disposable diaper 50 (a portion of which is shown in FIG. 2), the orientation of the fibers 36 in the nonwoven web 30 relative to the edges of the diaper 50 is also important. In such a case, the fibers 36 of the nonwoven web 30 are preferably primarily oriented in a single direction (as shown in FIG. 7) so that they generally parallel to the longitudinal edges 60 of the diaper 50.

Such an orientation of the fibers 36 in the nonwoven web 30 provides the greatest resistance to the disengagement of the hooks 28 when the fastening device 20 is subjected to the forces typically exerted on a diaper fastening system. These forces are usually applied in the plane of the interface between the fastening components in a direction parallel to the end edges of the diaper. The orientation of fibers 36 referred to above can be contrasted with the situation in which the fibers 36 are perpendicular to the longitudinal edges 60 of the diaper 50. In this latter less desirable case, the fibers 36 would run in the same direction as (or parallel to the direction of) such forces. In the latter case, the fibers 36 may not be as able to serve as a "catch" for the hooks 28 of the mating hook component 24.

In other alternative embodiments (such as that shown in FIGS. 1-3), particularly when a more lofted nonwoven web 30 is required, the fibers 36 may be randomly oriented. If the fibers 36 of the nonwoven web 30 are randomly-oriented, the fibers 36 will "criss-cross" and stack upon one another to create loft (or height). This will provide additional space for the hooks 28 of the mating hook component 24 to occupy when the hook component 24 engages the nonwoven female component 22.

The orientation of fibers 36 in the nonwoven web 30 can be analogized to an arrangement of logs. If several logs are laid side-by-side, the height of the group of logs will be only equal to the diameter of the logs. However, if the logs are oriented in different directions, e.g., if they are stacked (for instance, as in a log cabin), the height of the stack would be equal to the sum of the diameters of the stacked logs.

The fibers 36 in the nonwoven web 30 may preferably also be crimped for additional loft. The term "crimped", as used herein, means that the fibers 36 are wavy or bent along their lengths. The fibers 36 may be crimped (preferably before carding, or the like (the fibers of spunbonded webs will not usually be crimped, however)) by any suitable commercial crimping process. The fibers 36 in such a nonwoven web 30 preferably have at least about 10 crimps/inch (about 4 crimps/cm.), and more preferably at least about 14 crimps/inch (an average of about 5.5 crimps/cm.).

The fibers of the nonwoven web 30 can be comprised of any suitable material, including, but not limited to polyesters (such as polyethylene therapthalate (or PET)), polyethylene, and polypropylene, or any combinations of these and other suitable materials known in the nonwoven fabric industry. For example, the nonwoven web 30 could comprise a mixture of fibers of two different types of materials (e.g., a mixture of polyester and polypropylene fibers). In still other cases, the nonwoven web 30 could be comprised of fibers that are comprised of more than one material (e.g., a polyester fiber coated with polypropylene). Suitable polypropylene fibers for such a nonwoven web include those available from the Hercules, Inc. of Wilmington, Del. as product numbers T-181, T-182, and T-196.

The amount of inter-fiber bonding between the fibers 36 of the nonwoven web 30 is important to the female component 22 of the present invention. The bond sites created by the bonds 42 between the fibers 36 in the nonwoven web 30 will tend to reduce any spreading of fibers 36 to accommodate the hooks 28. In addition, an excessive number of inter-fiber bonds 42 in the nonwoven web 30 will interfere with the entry of the hooks 28.

The quantity of inter-fiber bonding depends on the type of nonwoven material used when the female component 22 is manufactured. The nonwoven web 30 used could be initially unbonded and then later bonded during the process of manufacturing the female component 22. For instance, the female component 22 could be made by bonding an unbonded layer of loose fibers to a backing material, in which case there may be no inter-fiber bonds 42.

It may be preferred for ease of manufacturing, however, that a commercially-available pre-bonded web be used. In such a case, this web will be bonded to the backing 34. If the female component 22 is made from a pre-bonded nonwoven web, there will be a certain amount of inter-fiber bonding. In this latter case, the inter-fiber bonds should occupy less than about 10%, preferably less than about 6%, and most preferably less than about 2½% of the area of the nonwoven web. This will assure that the space occupied by the inter-fiber bonds 42 will not interfere with the penetration of the hooks 28 of the mating hook component 24.

The percentage of inter-fiber bonding is preferably measured by examining a representative sample of the nonwoven web 30 under a microscope. (The following method is preferably also used to measure the percentage of area occupied by the bonds between the nonwoven web 30 and the backing 34. In the latter case, however, the characteristics of a sample of the entire female component 22, rather than just the nonwoven web 30, are examined.) The sample examined should be 4 inches×4 inches (about 10.2 cm.×about 10.2 cm.). The sample is viewed under the microscope from directly above the side that forms the first surface 31. The plan view area of each of the inter-fiber bonds 42 present throughout the entire thickness of the sample is measured. The areas are calculated after the size of the bonds 42 are measured using any accurate scale provided on the lens of the microscope.

The sum of the areas of the bonds 42 is divided by the area of the sample. The result is expressed as a percentage. This is the percentage of area occupied by the inter-fiber bonds 42. For the purposes of the present invention, if the percentage in any one square inch (6.5 square centimeter) section of the sample falls within the ranges specified herein, the material in issue will be considered to fall within the specified range.

The nonwoven web 30 is also, preferably resilient. A resilient nonwoven web 30 is especially desirable when the fastening device is used on a disposable absorbent article. This will allow the nonwoven web 30 to continue to maintain space for the hooks 28 to occupy, even after the nonwoven female component 22 has been compressed during manufacturing, packaging, and in use, and the like.

The material used in the nonwoven web 30 should, preferably, be relatively soft if the female component 22 is used in a fastening system on a disposable absorbent article, so that the female component 22 will be comfortable for the wearer in the event it contacts the wearer's skin.

The nonwoven web 30 can be made soft by providing the nonwoven web 30 with a "skin friendly" surface. This can be done in a number of ways. For instance, as shown in FIG. 4, the nonwoven web 30 can be provided with a certain amount of relatively low denier (e.g. between about 0.5 to about 5 denier. preferably about 3 denier) fibers along its first surface 31. Because these lower denier fibers 30a that overlie higher denier fibers 30b are finer, they will present a softer, less coarse surface for the wearer. The finer fibers can be arranged in any suitable form at the first surface 31, including, but not limited to in the form of a layer.

The nonwoven web 30 can be produced by many different processes. For example, the nonwoven web could be either a carded or a spunbonded web. Such nonwoven webs can be made by any suitable commercial carding or spunbonding processes.

Suitable materials for such a nonwoven web 30 can be obtained in the form of a carded nonwoven web from Veratech Nonwoven Group of the International Paper Company of Walpole, Mass. 02081 by specifying the desired characteristics described herein (such as basis weight, fiber denier and composition). (The inter-fiber bonding in the fabric, however, generally must be measured as described above.) An example of a suitable carded nonwoven web useful in other embodiments of the female component 22 can include materials that have been used as topsheets in diapers and other disposable absorbent articles (provided they have the characteristics described herein). Suitable spunbonded nonwoven webs can be obtained from the Nonwovens Division of the James River Corporation located in Simpsonville, S.C. (It is expressly not admitted, however, that any of the materials described herein are known to have been used in fastening devices.)

The backing 34 is positioned beneath the nonwoven web 30. The backing 34 provides a foundation for the nonwoven web 30. The backing 34 serves as a surface to which the nonwoven web 30 can be affixed. The backing 34 is optional, however. For instance, in an alternative embodiment of the female component 22, there is no backing and the nonwoven web 30 can be bonded directly to the substrate (the surface of the article to which the female component 22 is to be attached), and the substrate will serve the function of the backing.

Figure 8:
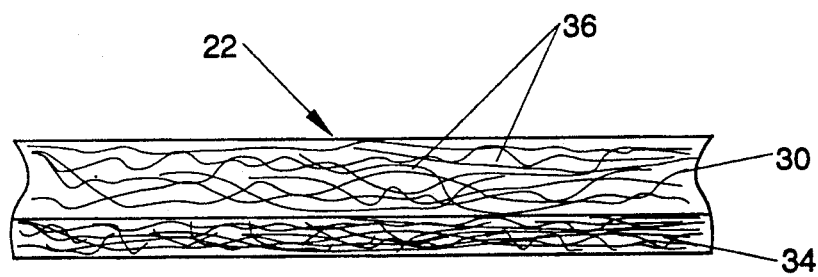
FIG. 8 is a simplified side view of an alternative embodiment of the nonwoven female component of the present invention in which the backing is a nonwoven web.
Figure 9:
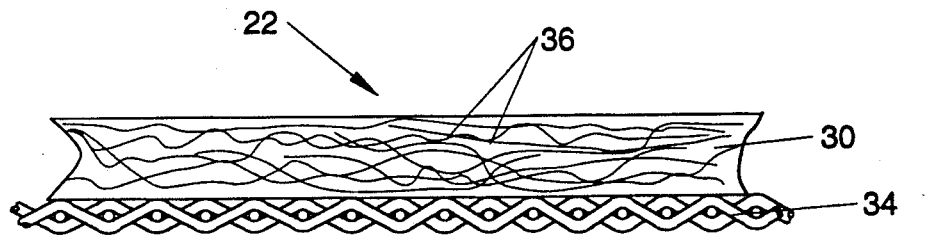
FIG. 9 is a simplified side view of an alternative embodiment of the nonwoven female component of the present invention in which the backing is a woven fabric.

Many types of material are suitable for use as the backing 34. The backing 34 preferably should be some type of material that the hooks 28 of the mating hook component 24 will not penetrate. The backing 34 could be a film, another nonwoven web as shown in FIG. 8, or a woven fabric as shown in FIG. 9. The backing 34 is generally a layer of material. Typically, the backing 34 will be a film. The backing 34 can be made of polyester, polyethylene, or polypropylene, or any other suitable material. Suitable materials for use as the backing 34 include any commercially-available low gauge (e.g., from about 0.75 to about 3 mil (about 0.02 mm. to about 0.08 mm.)) polyester, polyethylene, or polypropylene film. Suitable polypropylene film can be obtained as the product designated JR-136 from the Food and Consumer Packaging Group of the James River Corporation of Cincinnati, Ohio.

If the substrate comprises the backsheet of a disposable diaper, the layer that takes the place of the backing may be comprised of any of the above materials, or similar materials. Typically, however, such a backsheet will be comprised of polyethylene.

The nonwoven web 30 can be secured to the backing 34 in any suitable manner.

Preferably, for ease of manufacture, the nonwoven web 30 is autogenously secured to the backing 34. The term "autogenously", as used herein, means that the nonwoven web 30 is secured to the backing 34 without the aid of a third material. Thus, the nonwoven web 30 can be fused or melted into the backing 34.

The means used to hold the nonwoven web 30 and the backing 34 together (bonding means 44) must have several characteristics. The bonding means 44 must not occupy so much space that it interferes with the spaces needed for the hooks 28 of the mating hook component 24 to penetrate and occupy within the nonwoven web 30.

The bonds between the nonwoven web 30 and the backing 34 should be such that after the female component 22 has been manufactured, the total plan view area occupied by both any inter-fiber bonds 42 and the bonds between the nonwoven web 30 and the backing 34 (the "total bonded area", or simply the "total area") is less than about 35%, more preferably, between about 10% and about 35%, most preferably between about 10% and about 18% of the area of the female component 22. The total bonded area is measured in the same manner as specified above for measuring the percentage of space occupied by the inter-fiber bonds 42. (The area of the bonded regions 46 is also included in the calculations, however.)

The bonding means 44 must also be sufficiently strong that the entire nonwoven web 30 will not separate from the backing 34 when the hooks 28 are disengaged. The bonding means 44 may form bonded regions, bonded areas, 46 that are either stronger or weaker than the fibers 36 that comprise the nonwoven web 30. In preferred embodiments of the present invention, the bonded areas 46 are sufficiently strong relative to the strength of the fibers 36 of the nonwoven web 30 that when relatively stiff hooks are used, the fibers 36 of the nonwoven web 30 will fail instead of being pulled loose at a bond site.

Figure 4A:
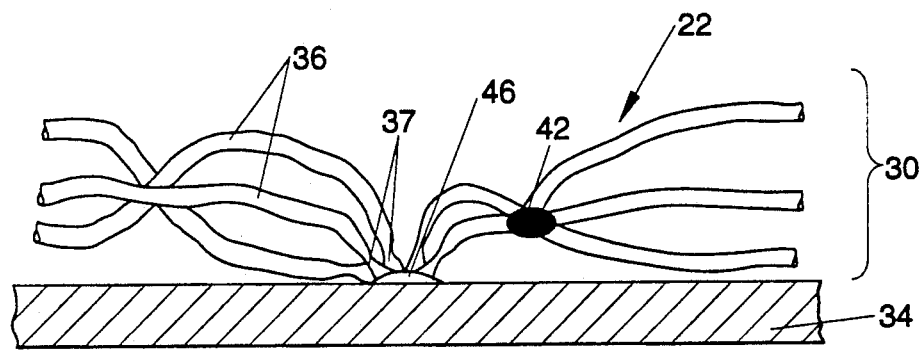
FIG. 4A is a greatly enlarged side view of an embodiment of the female component which shows the thinning of the fibers of the nonwoven web at a bond site.

This type of strength can be imparted in the bonded areas 46 in the following manner. When the nonwoven web 30 is autogenously bonded to the backing 34, the fibers 36 of the nonwoven web 30 will be "necked down" (will become thinner) at those places designated 37 in FIG. 4A where they are bonded to the backing 34. That is, the fibers 36 will be thinner adjacent the individual bonded areas, bond sites 46, than at other places along the lengths of the fibers. This results because some of the material that comprises the fibers 36 will be melted to form the bond. This will decrease the diameter of the fiber 36 near the bond site. Typically, in such instances, the fibers 36 will fail near a bond site 46 at the necked down portions 37.

This type of structure (one in which the bonded areas 46 is stronger than the fibers 36 of the nonwoven web 30) is preferred over structures in which the bonded areas 46 are weaker than the fibers 36 comprising the nonwoven web 30. In the case of the former, if rigid hooks are used, the hooks 28 will usually become disengaged by a failure of a fiber 36 near a bond site 46 rather than relying on the hooks 28 bending to release the fibers 36. In the preferred type of structure, only one fiber 36 will typically be broken when a hook 28 is disengaged. This will result in only a minimal disruption of the female component 22 upon disengagement of the hooks 28. There will still be a significant number of fibers 36 to catch the hooks 28 the next time the fastening device 20 is closed.

If, on the other hand, the bond sites 46 are the weakest element of the female component 22, each rigid hook 28 may be able to break several bond sites 46 when the fastening device 20 is opened. This could cause entire fibers 36 of the nonwoven web 30 to be either nearly or completely torn away from the backing 34. If that occurs, the number of secured fibers 36 available to engage the hooks 28 will be significantly reduced. In addition, such loose fibers will tend to interfere with the open space needed for the hooks 28 of the mating hook component 24 to penetrate.

The possible types of bonding means 44 may include, but are not limited to ultrasonic bonds, heat/pressure bonds, and adhesive bonds.

The type of bonding means 44 used may be limited to some extent by the types of materials used for the nonwoven web 30 and the backing 34. This is particularly true if the bonding means 44 are ultrasonic or heat/pressure bonds. When these two types of bonding means 44 are used, the materials comprising the nonwoven web 30 and the backing 34 should be compatible as far as the type of material and the melting temperature of the same are concerned. Thus, the term "compatible", as used herein, means that the materials are capable of being fused together.

When materials are described herein as being "similar", it is meant that the materials are generally comprised of the same compound, such as polypropylene. Similar materials may, however, comprise two different types of such a material (for instance, two different polypropylene materials).

The pattern that the bonded areas 46 are arranged in is also important. The bonding pattern may be either continuous or some suitable type of intermittent pattern. Some of the bonding patterns disclosed in U.S. patent application Ser. No. 07/355,065 entitled "Loop Fastening Material for Fastening Device and Method of Making Same" filed in the name of John R. Noel, et al. on May 17, 1989, may be suitable, provided the bonding pattern meets the criteria set forth herein.

A continuous bonding pattern is often preferred so that the fibers 36 in the nonwoven web 30 will be more likely to be properly secured in place.

An intermittent pattern that provides relatively small spaces or breaks between bonded areas 46, however, should also be suitable. A non-limiting example of an intermittent bonding pattern is provided in the upper left hand corner of FIG. 7 for purposes of illustration. The breaks 46' between the bonded areas 46 of such an intermittent pattern should be sufficiently small that there will be relatively few fibers 36 in the nonwoven web 30 with unbonded loose ends. It is believed that an intermittent bonding pattern which has breaks 46' between bonded areas 46 that are less than or equal to the diameter of the smallest diameter fibers used in the nonwoven web will be suitable. Larger breaks 46' between bonded areas 46 may also be suitable. For instance, in some cases, the breaks 46' between bonded areas 46 could be as large as 1½ times, or even 5 times (or possibly even larger) the diameter of the smallest diameter fibers in the nonwoven web 30.

If an intermittent bonding pattern is used, another important factor is the frequency of the breaks 46' in the pattern. The breaks 46' should not occur too frequently. If the breaks 46' occur too frequently, there will be too many fibers 36 with unbonded loose ends. It is preferred that the bonded areas 46 are longer (occupy more area) than the breaks 46' along each intermittent line in the bond pattern.

The pattern of the bonded areas 46 is preferably regular. Suitable bonding patterns include continuous or intermittent lines. Such lines can be curved, e.g., sinusoidal, or they can be arranged in the form of grids that define different geometrical shapes such as squares, rectangles, hexagons, diamonds, and circles. This will provide the female component 22 with relatively uniform holding characteristics.

The bonded areas 46 are preferably sufficiently close together that the fibers 36 of the nonwoven web 30 will have relatively few unbonded loose ends. In order to ensure that this happens, the distance between bonded areas 46 should preferably be less than the average length of fibers 36 in the nonwoven web 30, more preferably, less than or equal to about one-half the length of the fibers 36 in the nonwoven web 30. (The distance between bonded areas 46 specified refers those spaces other than the breaks 46' in an intermittent bonding pattern.)

A preferred bonding pattern is the diamond-shaped pattern shown in FIG. 7. The "diamonds" in the "diamond-shaped" pattern are generally square elements. These elements are rotated approximately 45 degrees to give them the appearance of diamonds. The dimensions of the pattern should be such that the distance between bonded areas 46, in at least some portion of the area between bonded areas, is greater than the projected plan view dimensions of the heads 38 of the hooks 28 of the mating hook component 24.

Examples of diamond-shaped bonding patterns which are suitable for a female component 22 that can be used with some of the hook components described herein are as follows. These include, but are not limited to patterns having sides that measure about ¼ inch×¼ inch (about 0.6 cm.×0.6 cm.); about ⅜ inch×⅜ inch (about 1 cm.×1 cm.); about ½ inch×½ inch (about 1.3 cm.×1.3 cm.); and, about ¾ inch×¾ inch (about 2 cm.×2 cm.).

The width of the bonded areas 46 in cross-section, $B_w$, shown in FIG. 7, can vary. In the examples of the diamond-shaped bonding patterns described above, a suitable bond width (measured at the backing 34) is between about 0.03 inch and about 0.05 inch (about 0.76 mm. and about 1.3 mm.).

The cross-sections of the bonded areas 46 shown in FIG. 3 are shown to be tapered in width so that they become narrower from the first surface 31 of the female component 22 to the second surface 33. The tapering of the width of the bonds in cross-section is primarily of interest in relation to the cost and life of the patterned rolls used to form such bonds in the method of making the female component 22. (For instance, it may be less expensive to manufacture rolls having patterned surfaces tapered to form such bonds.)

It should be understood that the embodiments of the nonwoven female component 22 of the present invention shown in the drawings are for purposes of illustration only. It is apparent that there are many possible combinations of the different types of nonwoven webs and backings described herein. These combinations are capable of being understood from the description provided above and the examples set forth in the drawings. The nonwoven female component 22 is, thus, not limited to the specific embodiments shown in the drawings.

The present invention, thus, provides a low-cost female component for a refastenable fastening device. The female component 22 comprises a nonwoven web 30 with characteristics specifically suited to receive the hooks 28 of a mating hook component 24. The fibers 36 of the nonwoven web 30 serve to entangle the individual hooks 28 of the mating hook component 24. The female component 22 does not require loops of material to be specifically formed to engage the hooks of a mating hook component. The female component of the present invention, thus, does not have the relatively high cost of conventional loop components.

As a result, the fastening device 20 is especially useful on such disposable articles as packaging, disposable absorbent articles, disposable wraps, and the like. The female component 22 is more suited for disposable articles since the fastening device on a disposable article is opened and closed far fewer times than on reusable articles. The female component 22 generally only needs to be strong enough to provide a limited number of secure closures (a maximum of 10-20).

It should be noted, however, that the female component 22 can be made much stronger for use on durable articles or for any other contemplated use. This can be done by, for example, increasing the diameter or denier of the fibers 36, more strongly securing the fibers 36 to the backing 34 or increasing the density of the fibers 36 relative to the number of hooks 28. However, these changes also increase the cost of the female component 22.

There are other characteristics of the fastening device that could also be varied in other embodiments. For instance, if the hook component 24 has sufficiently resilient individual hooks 28, a female component 22 having smaller diameter fibers, or weaker fibers, may be used. In these cases, the hooks 28 may open to disengage from mechanical entanglement with the fibers 36 of the nonwoven web 30 before those fibers 36 break. That is, the hooks can serve as a "release mechanism" to open the fastening device.

The female component 22 can also be used in conjunction with lower cost hook components having more brittle hooks. In such cases, the fibers 36 of the nonwoven web 30 may advantageously serve as a "failure mechanism" to allow the disengagement of the hooks 28 upon opening the fastening device.

3. The Mating Hook Component

The mating hook component 24 is shown in numerous places in the drawings.

The term "hook component", as used herein, as used to designate the portion of the fastening device 20 having engaging elements, such as hooks 28. The term "hook" is non-limiting in the sense that the engaging elements may be in any shape known in the art so long as they are adapted to engage a complementary loop fastening material or the female component 22 of the present invention.

The hook component 24 comprises a base 26 having a first surface 27 and a second surface 29 and a plurality of engaging elements 28 extending from the first surface 27 of the base 26. Each of the engaging elements 28 are shown to preferably comprise a stem 40 supported at one end on the base 26 and an enlarged head 38 positioned at the end of the stem 40 opposite the base 26.

The hook components 24 used with the nonwoven female component 22 of the present invention can be conventional, commercially available hook materials. The hook component 24, however, is not limited to conventional materials with flexible, resilient hooks. Suitable hook components can have less expensive, relatively inflexible, more brittle hooks.

The hook components 24 used with the nonwoven female component 22 can have hooks 28 with blunt heads 38. The portion of the heads 38 of the hooks 28 that are blunt is that portion designated as the apex 39 of the hook 28 in FIG. 6. The apex 39 will first come in contact with the female component 22 of the present invention when the female component 22 and the complementary hook component 24 are placed in face-to-face relationship with each other. This portion is referred to as the apex of the hook 28 because it is portion of the hook 28 that is greatest perpendicular distance from the base 26 of the hook component 24. The term "blunt", as used herein, means that the apex 39 is dull in that it forms an edge or point that is not sharp. The apex 39 of a hook 28 having a blunt head can be generally rounded, flat, or any other shape that does not provide a sharp point.

The female component 22 of the present invention, thus, does not require specially-made rigid, sharp hooks to be used. It is, however, possible for hooks of all configurations, including such sharp hooks to be used with the female component 22.

A suitable hook component 24 may comprise a number of shaped engaging elements projecting from a woven backing such as the commercially available material designated "Scotchmate" brand No. FJ3402 available from Minnesota Mining and Manufacturing Company, St. Paul, Minn. The engaging elements may have any shape known in the art such as hooks, "T's", mushrooms or any other shape. A particularly preferred hook component is described in U.S. Pat. No. 4,846,815 entitled "Disposable Diaper Having An Improved Fastening Device" which issued to C. L. Scripps on Jul. 11, 1989. Another particularly preferred hook component is described in European Patent Application Publication Number 0 381 087 A1 entitled "Refastenable Mechanical Fastening System and Process of Manufacture Therefor", published Aug. 8, 1990 by Dennis A. Thomas. The disclosure of these patent publications and all other patents, patent applications, and publications referred to in this application are hereby incorporated by reference herein.

(It should be understood that the various portions of the hook components may be described in these references with slightly different terminology than is used herein. However, the drawings and elements contained herein can be compared to those of the references to readily locate the corresponding portions of the hook components described in those publications.)

The hook component 24 may be manufactured from a wide range of materials. Such suitable materials include, but are not limited to nylon, polyester, polypropylene, or any combination of these or other materials.

The size of the heads 38 of the hooks 28, as noted above, determines the open space required between the fibers 36 of the nonwoven web 30. Some non-limiting examples of sizes of hooks 28 that are useful with the female component 22 of the present invention are provided below.

One suitable hook component 24 has T-shaped hooks 28 with the following dimensions. The length of the head 1, is about 1 mm.; the width w, is about 0.2 mm.; and the height $h_1$, is about 0.3 mm. If this type of hook component is used, the openings between the fibers 36 of the nonwoven web 30, should be (or should readily spread without being pierced to) dimensions of slightly greater than about 0.2 mm by about 1 mm. The caliper of the nonwoven web 30 should be greater than about 0.3 mm.

Another suitable hook component 24 has hooks 28 in the shape of an upside down letter "J". (The hooks 28 of such a hook component 24 could also be said to resemble candy canes.) In other variations, such a hook could resemble an upside down upper case letter "L". Such hooks could have the following dimensions. The length of the head 1, is about 0.5 mm.; the width w, is about 0.2 mm.; and the height $h_1$, is about 0.3 mm. Thus, if this type of hook component is used, the openings between the fibers 36 of the nonwoven web 30, should be (or should readily spread without being pierced to) dimensions of slightly greater than about 0.2 mm. by about 0.5 mm. The caliper of the nonwoven web 30 should be greater than about 0.3 mm.

Still other hook components 24 could have hooks that are as small as ½ to ¼, or smaller than the hooks described above.

4. Examples of Uses of the Refastenable Fastening Device

The fastening device 20 of the present invention is especially useful as a fastening device for disposable articles, particularly disposable absorbent articles.

The term "disposable absorbent article", as used herein, refers to articles which absorb and contain body exudates. More particularly, the term refers to articles which are placed against or in proximity to the body of the wearer to absorb and contain the various exudates discharged from the body. The term "disposable" means that such articles are intended to be discarded after a single use (i.e., they are not intended to be laundered or otherwise reused). Examples of disposable absorbent articles include diapers, incontinent garments, sanitary napkins, bibs, bandages, and the like.

Figure 10:
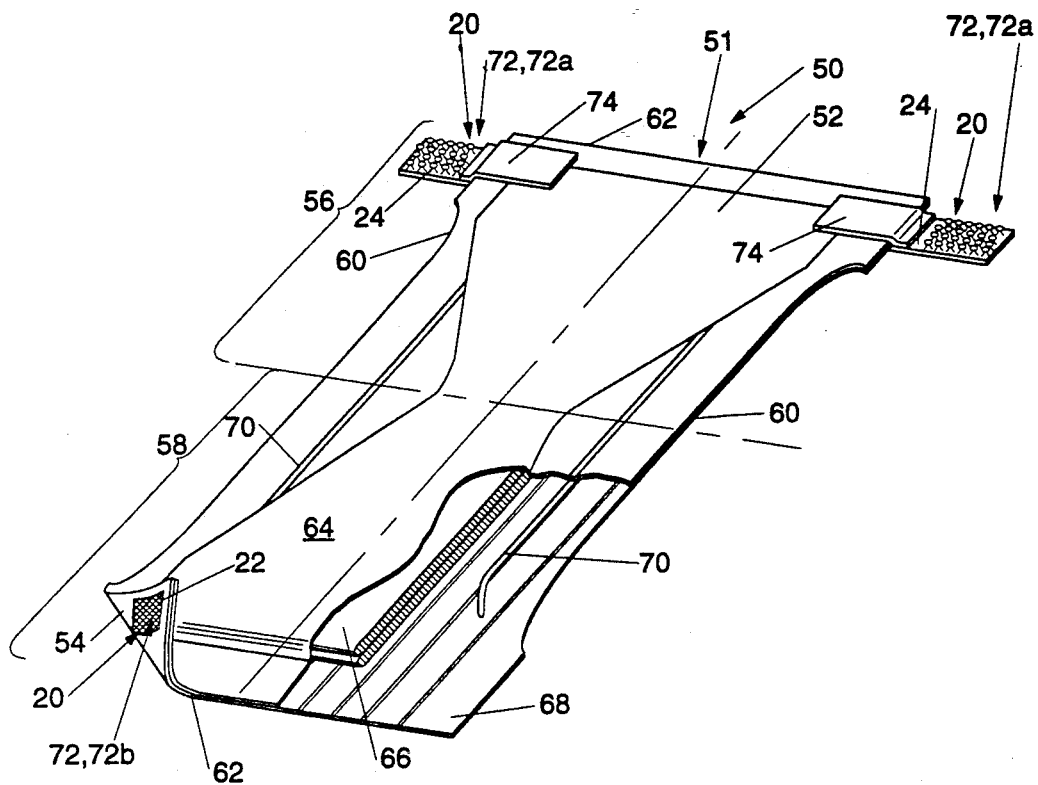
FIG. 10 is a partially cut-away perspective view of a disposable diaper that includes the fastening device of the present invention.

The fastening device 20 is shown in FIG. 10 positioned on a preferred embodiment of a disposable absorbent article, disposable diaper 50. The term "diaper", as used herein, refers to a garment generally worn by infants and incontinent persons that is drawn up between the legs and fastened about the waist of the wearer.

The disposable diaper 50 has an inside surface (or body surface) 52, intended to be worn adjacent to the body of the wearer. The diaper 50 has an outside surface (or garment surface) 54 intended to be placed adjacent the wearer's clothing when the diaper 50 is worn. The diaper 50 has two waist regions, which are designated as first waist region 56 and second waist region 58. The diaper 50 has two spaced apart longitudinal edges 60 and two spaced apart transverse or end edges 62.

The disposable diaper 50 comprises a body portion 51 and a mechanical fastening system, such as tape fastening system, or simply "fastening system" 72. The body portion 51 of the diaper 50 comprises liquid pervious topsheet 64, an absorbent core 66, a liquid impervious backsheet 68, and elastic members 70. The topsheet 64, the absorbent core 66, the backsheet 68 and the elastic members 70 may be assembled in a variety of well known configurations.

Several examples of the kinds of diapers to which the present invention is readily adapted are shown in U.S. Pat. No. Re. 26,151 entitled "Disposable Diaper" which reissued to Robert C. Duncan, et al., on Jan. 31, 1967; U.S. Pat. No. 3,860,003 entitled "Contractible Side Portions For Disposable Diapers" which issued to K. B. Buell on Jan. 14, 1975; U.S. Pat. No. 4,695,278 entitled "Absorbent Article Having Dual Cuffs", issued to Michael I. Lawson on Sep. 22, 1987; U.S. Pat. No. 4,834,735 entitled "High Density Absorbent Members Having Lower Density And Lower Basis Weight Acquisition Zones" which issued to Miguel Alemany, et al. on May 30, 1989; and, U.S. Pat. No. 4,909,803 entitled "Disposable Absorbent Article Having Elasticized Flaps Provided With Leakage Resistant Portions" which issued to Mohammed I. Aziz, et al. on Mar. 20, 1990. It should be understood, however, that the fastening device 20 of the present invention is not limited to use with any specific diaper structure or configuration.

The fastening system 72 of the diaper 50 comprises the fastening device 20 of the present invention, among other elements. The fastening system 72 may be in the form of any of the well known configurations and constructions currently in use. Preferably, the fastening system 72 is a tab fastening system, preferably a tape tab fastening system.

The tape tab fastening system can comprise any of the well known tape tab configurations and constructions currently in use. A preferred tape fastening system uses the Y-tape tab described in detail in U.S. Pat. No. 3,848,594 entitled "Tape Fastening System For Disposable Diaper" which issued to K. B. Buell on Nov. 19, 1974. Alternatively preferred tape fastening systems are described in detail in European Patent Application 0 233 704-A, entitled "Disposable Diaper Having Wide Tapered Fastening Tapes" published Aug. 26, 1987 by H. R. Burkhart and Kenneth B. Buell; previously referenced U.S. Pat. No. 4,846,815 issued to C. L. Scripps; and U.S. Pat. No. 4,963,140 entitled "Mechanical Fastening Systems With Disposal Means for Disposable Absorbent Articles" which issued to Anthony J. Robertson, et al. on Oct. 16, 1990.

In still other preferred embodiments, the female component 22 of the fastening system 72 could comprise an element, such as a patch located on one of the surfaces of the body portion 51 of a diaper (or other suitable places) to form an "inner fastening member" as described in U.S. Pat. No. 4,699,622 entitled "Disposable Diaper Having An Improved Side Closure" which issued to J. W. Toussant, et al. on Oct. 13, 1987.

The tape fastening system 72 shown in FIG. 10 is a non-limiting example of the type of fastening system which can use the fastening device 20 of the present invention. The tape fastening system 72 comprises a tape tab 74 having a first fastening element 72a located thereon, and a second fastening element (or "landing member") 72b. The second fastening element 72b is mechanically engageable with the first fastening element 72a.

Preferably, the first fastening element 72a comprises the hook component 24. The hook component 24 provides hooks 28 that extend from the tape tab 74. In a preferred embodiment of the disposable diaper 50, the nonwoven female component 22 of the present invention comprises the second fastening element 72b. In other embodiments, the positions of the components of the fastening device 20 of the present invention could be reversed so that the first fastening element 72a comprises the nonwoven female component 22 and the second fastening element 72b comprises the hook component 24.

As shown in FIG. 10, the nonwoven female component 22 is preferably located on the second waist region 58 of the diaper 50. In a preferred embodiment of the disposable diaper 50, the fibers 36 in the nonwoven web 30 of the female component 22 are aligned in a single direction. The female component 22 is oriented so that the fibers 36 in the nonwoven web 30 extend essentially parallel to the longitudinal edges 60 of the diaper 50. This orientation aligns the fibers 36 generally perpendicular to the direction of shear forces applied to the fastening device 20 during use. In this configuration the fibers 36 provide the maximum peel and shear force resistance. The female component 22 may, however, be oriented on the second waist region 58 in any manner with the fibers 36 extending in any direction.

In use, the diaper 50 is applied to the wearer by positioning the first waist region 56 under the wearer's back and drawing the remainder of the diaper 50 between the legs of the wearer so the second waist region 58 is positioned across the front of the wearer. The tape tabs 74 are then positioned adjacent to the female component 22 positioned on the outside surface 54 of the second waist region 58 so the hooks 28 disposed on the tape tab 74 will engage the female component 22 to form a side closure.

Method of Making the Female Component

Figure 11:
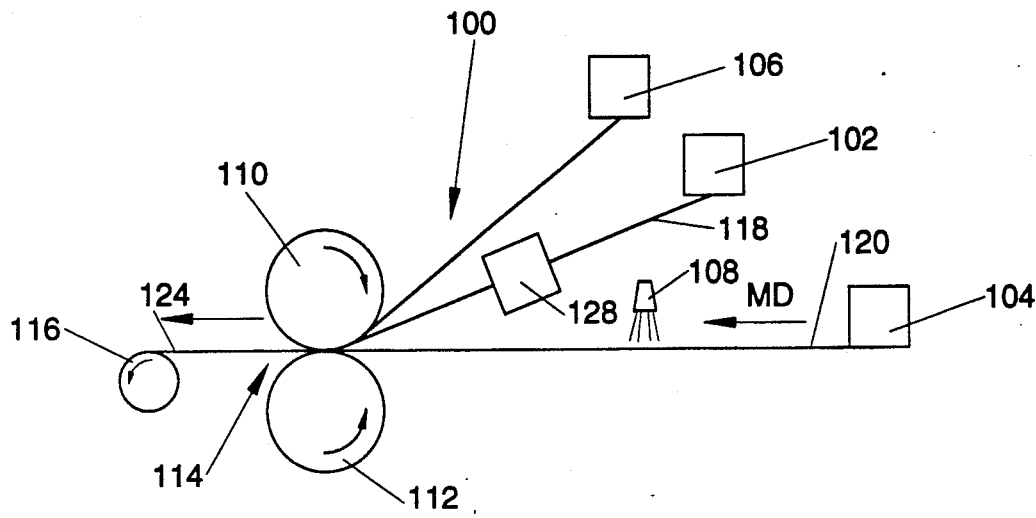
FIG. 11 is a schematic side view of a process for making the female component of the present invention.

The method or process of making the female component 22 of the present invention is shown in schematic form in FIG. 11.

The apparatus for making the nonwoven female component 22 of the present invention is designated 100. The apparatus 100 includes a first supply means 102 and a second supply means 104. The supply means 102 and 104 feed into the system the materials that will comprise the nonwoven web 30 and the backing 34 of the nonwoven female component 22.

The apparatus 100 may also include an element that provides an embossed surface, such as embossed roll 110 (which may be patterned), and an anvil member, such as anvil roll 112. The embossed roll 110 and anvil roll 112 define a nip 114 between them. The nip 114 is where the laminae of the webs or other materials fed into the system are bonded together. The bonded web 124 may then travel to a take-up roll 116, where it is wound for subsequent use. The individual parts of the apparatus 100 are described more fully below.

In the apparatus 100 shown in FIG. 11, the preferred method of making the nonwoven female component 22 involves feeding the materials for the nonwoven web and the backing into the system and and bonding the same. The materials may be bonded by various different methods, including, but not limited to by adhesives, ultrasonics, and by heat/pressure processes.

The preferred method of bonding the materials together is by passing the composite of the materials between two heated rolls, one of which has a pattern on its surface, and impressing the bond pattern into the materials. One method of heat/pressure bonding that could be used is described in U.S. Pat. No. 4,854,984 issued to Ball, et al. on Aug. 8, 1989 (provided the patterned cylinder described therein forms bonded areas that meet the criteria set forth in this description).

The first supply means 102 feeds a first material 118 used for the nonwoven web 30 into the system. The first material 118 can be any of those materials specified as being suitable for use in the nonwoven web 30 in Section 2 of this description. Thus, the first supply means 102 could be any conventional means used to introduce a material into a laminating process. The first supply means 102 could be, but is not limited to an unwind roll; a web or fabric producing machine, such as a conventional carding machine, spunbonding machine; or a hopper for feeding a layer of loose fibers into the system.

In the preferred embodiment of the process of the present invention, the first supply means 102 comprises either a supply of spunbonded fibers or a conventional machine for producing the same. Preferably, the first supply means 102 feeds a layer of loose (i.e., unbonded) continuous length fibers into the system. These loose fibers are, preferably, uniformly deposited onto a suitable surface. The fibers could be deposited onto a surface such as the material described below that will comprise the backing 34. In other alternative embodiments, rather than being in the form of a layer of loose fibers, the first material 118 could be in the form of a web of entangled fibers or a web of bonded fibers.

Preferably, the material 118 used to form the nonwoven web 30 will have sufficient thickness or loft built into its structure to accommodate the hooks of the mating hook component. If not, it is contemplated that the material 118 used to form the nonwoven web 30 could be lofted during the process of making the female component. If that is the case, a means for lofting the material could be included in the apparatus. Such a means could include a conventional pleating or corrugating process (represented by block 128 in FIG. 11). However, a process that requires such an extra step is generally less preferred.

Regardless of the form in which the fibers used to form the nonwoven web 30 are fed into the apparatus, (whether it be in the form of a web, or in the form of loose, unbonded fibers), the fibers of the first material 118 are preferably oriented primarily in the machine direction. This will provide the female component 22 with fibers 36 having the desired single direction orientation that is preferred for holding the hooks of the mating hook component.

The term "machine direction" (MD) refers to that direction which is parallel to the flow of the materials 118 and 120 through the apparatus 100. The "cross-machine direction" (CD) is perpendicular to the machine direction. These directions are indicated by arrows in FIGS. 11 and 12.

The second supply means 104 feeds a second material 120, used for the backing 34 into the system. The second material 120 can be any of those materials specified as being suitable for use as the backing 34 in Section 2 of this description. Thus, the second supply means 104 could be any of the means used to introduce a material into a laminating process. The second supply means 104 could be, but is not limited to an unwind roll; or a web or fabric producing machine, such as a weaving machine, knitting machine, conventional carding machine, or a spunbonding machine.

The backing 34, as noted above, may be optional. If the backing 34 is eliminated, the function ordinarily served by the backing 34 may be performed by the substrate to which the female component 22 is attached. The second material 120 could, therefore, be a substrate, such as a material used for the backsheet of a disposable diaper.

In other alternative embodiments of the apparatus 100 shown in FIG. 10, additional optional supply means similar to those shown, such as third supply means 106, could be provided if it is desirable to construct a nonwoven female component of more than two materials. Such additional supply means could, for example, be used to make a nonwoven web 30 of multiple layers, or to make the alternative embodiment having the skin friendly layer described above. In still other alternative embodiments, one or more of the materials fed into the system could be folded to create more than one layer of such a material.

The element that provides the embossed surface can be in any suitable configuration. For example, it can be in the form of an embossing plate or in the form of a cylinder. Preferably, it is a patterned cylinder, such as patterned cylinder 110. The patterned cylinder 110 is used to bond the material 118 used to form the nonwoven web 30 to the backing 34. The pattern forms the bonded areas 46 on the female component 22. The pattern should be in relief so that only a relatively small portion of the first material 118 will be compressed during the process. The remainder of the first material which will form the nonwoven web 30 should not be compressed so that the overall lofted character of the first material 118 will be maintained.

The pattern must form a bond with the characteristics described in Section 2 above. Thus, the space between the bonded areas 46 must be sufficient so that the hooks 28 of the mating hook component 24 can easily penetrate the nonwoven web 30. The space between the bonded areas 46 should not be so large in relation to the length of the fibers used to form the nonwoven web 30, however, that there are an inordinate number of fibers with unbonded loose ends.

Figure 12:
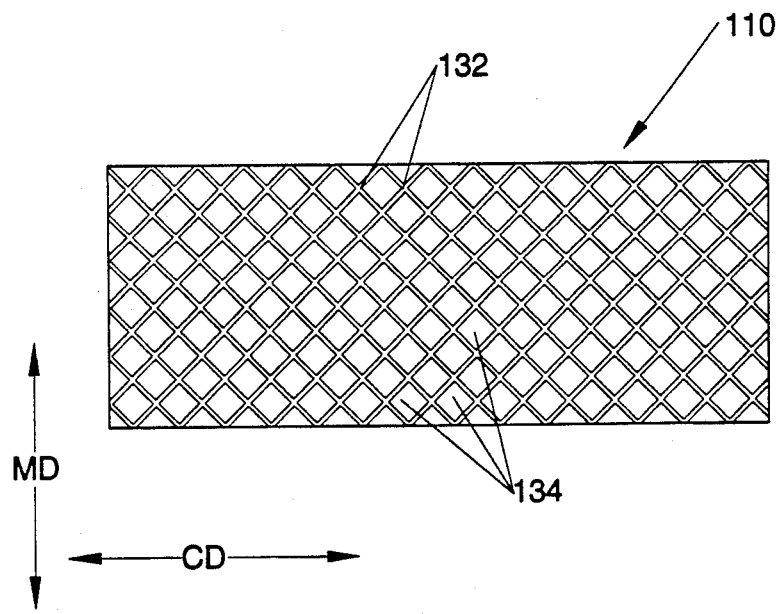
FIG. 12 is a schematic front view of one type of patterned roll that can be used in the process shown in FIG. 11 (the dimensions of the pattern being greatly enlarged for purposes of illustration).

The surface of the patterned roll 110 is shown in greater detail in FIG. 12. The surface defines lands 132 and recesses 134. The lands 132 and recesses 134 of the roll 110 have several characteristics. These include roll depth or depth of the recesses, dimensions of the pattern, etc. These characteristics will vary depending on the materials used for the nonwoven web 30 and backing 34 and on the type of bond pattern desired.

The patterned roll 110 shown in FIG. 12 is used to form the preferred diamond-shaped bond pattern shown in FIGS. 1–3.

The depth of the recesses 134 (or the height of the lands 132) should generally be greater than the sum of the caliper of the first material 118 and any other materials used to form a nonwoven web of multiple layers. Typically, the depth of the recesses is about 1½ times the sum of the calipers of such materials.

The patterned roll 110 has lands 132 that are essentially square shapes that have been rotated approximately 45 degrees with respect to the cross machine direction. These squares can have any suitable dimensions. For instance, these squares can be ¼ inch×¼ inch (about 0.6 cm.×0.6 cm.); about ⅜ inch×⅜ inch (about 1 cm.×1 cm.); about ½ inch×½ inch (about 1.3 cm.×1.3 cm.); and, about ¾ inch×¾ inch (about 2 cm.×2 cm.) to form the bonds described in Section 2 above. The width of such lands 132 can, for example, be between about 0.03 inch and about 0.05 inch (about 0.76 mm. and about 1.3 mm.).

The embossed roll 110 may be, and preferably is, heated. The temperature to which the rolls, such as embossed roll 110, are heated depends on the materials used to form the nonwoven web 30 and the backing 34. In the preferred embodiment shown, the first and second materials 118 and 120 are comprised of polypropylene. When polypropylene is used, the embossed roll 110 is preferably heated to a temperature of between about 155° C. and about 168° C.

The anvil member is preferably a cylinder with a smooth, surface, such as anvil roll 112. Preferably, the anvil roll 112 is also heated. Preferably, the anvil roll 112 is heated to a temperature of between about 104° C. and about 110° C. when polypropylene materials are used to form the female component 22. The anvil roll 112 rotates in the opposite direction as the embossed roll 110 (in other words, the two rolls are counter-rotating).

The first and second materials 118 and 120 are bonded together when they pass through the nip 114. The materials are bonded together by the application of heat and pressure from the rolls 110 and 112 at the nip 114. In one preferred embodiment of the process of the present invention, the rolls rotate so that the bonded web 124 is formed at a rate of about 100 feet/minute (about 30.5 meters/minute). The rolls exert a pressure of between about 300 and about 400 pounds per linear inch (between about 50 and about 70 kg./linear cm.) as measured across the nip in the cross-machine direction.

In alternative embodiments of the process of making the female component of the present invention, adhesives can be used to bond the materials 118 and 120 together instead of heat or heat and pressure. In an adhesive bonding process, adhesive could be applied by any suitable commercial adhesive supply means 108. Preferably, the adhesive supply means applies adhesive in a pattern similar to that formed by the lands 132 of the patterned roll 110. In such adhesive bonding processes, the patterned roll 110 could be replaced with a second smooth roll. However, in most cases it is preferable that the patterned roll 110 still be used so that all of the first material 118 is not compressed and the lofted character of the first material 118 is maintained. Such adhesive bonding processes, could be conducted without the application of pressure. Preferably, however, in such cases pressure is also applied with the rolls.

In still other alternative embodiments, the rolls 110 and 112 could be replaced by a commercially available ultrasonic welding device.

The rewind roll 116 collects the bonded web 124 of female component material. The roll of female component material can be taken from the rewind roll 116 and can be cut into appropriate sizes for use in a refastenable fastening device with a suitable hook component. For example, the cut pieces of the female component material can be bonded onto a disposable diaper. In other alternative embodiments of the process of the present invention, the rewind roll 116 could be eliminated, and the bonded web 124 could be fed directly into the appropriate place of a diaper manufacturing line. The bonded web 124 could be cut and affixed directly to the appropriate places on a web of diaper material.

The nonwoven female component 22 can, thus, be made relatively inexpensively in comparison to conventional loop materials. This process eliminates the need to loft or manipulate a material to form individual loops. The process results in a lower cost female component because the female component can be produced by a lower cost and relatively straight-forward bonding or laminating process, rather than the conventional weaving, knitting, pleating, or corrugating processes.

While particular embodiments of the present invention have been illustrated and described, it would be obvious to those skilled in the art that various other changes and modifications can be made without departing from the spirit and scope of the invention. It is to be understood that all of the limits and ranges specified in the foregoing description of the fastening device include all narrower ranges and limits that are within the specified limits and ranges. Thus, for example if a range is specified as being between about 6 and about 42 $g/m^2$, all narrower ranges, such as between about 10 and about 40 $g/m^2$, and between about 20 and about 30 $g/m^2$, etc, may be claimed even though these ranges are not separately listed. It is therefore intended to cover in the appended claims all such changes and modifications that are within the scope of this invention.

What is claimed is:

1. A female component for a refastenable fastening device, said female component having a planar outwardly facing surface capable of engaging a complimentary hook fastening component which has a base with individual hooks having blunt heads extending outward from said base, said female component comprising:

a backing, and a non-woven fibrous web having a basis weight between about 6 and about 42 $g/m^2$ so that there is space between the fibers in said fibrous non-woven web to allow said hook fastening component to penetrate said nonwoven web, said nonwoven web comprised of a plurality of fibers, wherein the plan view area occupied by any inter-fiber bonds of said nonwoven web is less than about ten percent of the total area of said nonwoven web, said nonwoven web being secured to said backing by bonds so that the total plan view bonded area occupied by both any inter-fiber bonds of said nonwoven web and by the bonds between said nonwoven web and said backing is between about 10 percent and about 35 percent of the total area of the female component.

2. The female component of claim 1 wherein the nonwoven web has a basis weight of between about 12 and about 36 $g/meter^2$.

3. The female component of claim 2 wherein the nonwoven web has a basis weight of between about 18 and about 24 $g/meter^2$.

4. The female component of claim 1 wherein the plan view area occupied by any inter-fiber bonds of said nonwoven web is less than about six percent of the total area of said nonwoven web.

5. The female component of claim 4 wherein the plan view area occupied by any interfiber bonds of said nonwoven web is less than about 2½ percent of the total area of said nonwoven web.

6. The female component of claim 1 wherein the total plan view bonded area is between about 10 percent and about 18 percent of the total area of the female component.

7. The female component of claim 1 wherein the fibers in said nonwoven web have a denier of between about 0.5 and about 15.

8. The female component of claim 1 wherein the fibers in said nonwoven web have a denier of between about 2 and about 15.

9. The female component of claim 1 wherein the fibers in said nonwoven web have a denier of between about 3 and about 9.

10. The female component of claim 1 wherein the fibers in said nonwoven web have a denier of between about 3 and about 6.

11. The female component of claim 1 wherein said nonwoven web is secured to said backing by bonding means that form bonded areas that are spaced apart less than or equal to a distance of about ½ the length of the fibers in the nonwoven web.

12. The female component of claims 1 or 11 wherein said bonded areas are intermittent.

13. The female component of claim 12 wherein said intermittent bonded areas have breaks between said bonded areas, and said breaks are less than or equal to about 1½ times the diameter of the smallest diameter fibers in said nonwoven web.

14. The female component of claims 1 or 11 wherein said bonded areas are continuous.

15. The female component of claim 14 wherein said continuous bonds are disposed in a pattern.

16. The female component of claim 1 wherein said nonwoven web is carded, and is comprised of fibers that have lengths between about 1 cm. to about 13 cm.

17. The female component of claim 16 wherein said fibers have lengths between about 5 cm. to about 8 cm.

18. The female component of claim 1 wherein said nonwoven web is spunbonded, and is comprised of continuous length fibers.

19. The female component of claims 1 or 16 wherein fibers in said nonwoven web are crimped with a crimping frequency of at least about 4 crimps/cm.

20. The female component of claim 1 wherein the fibers in said nonwoven web are randomly oriented.

21. The female component of claim 1 wherein the fibers in said nonwoven web are primarily oriented in a single direction.

22. The female component of claim 1 wherein said nonwoven web is resilient.

23. The female component of claim 1 wherein said backing comprises a film.

24. The female component of claim 1 wherein said backing comprises a nonwoven web.

25. The female component of claim 1 wherein said backing comprises a woven fabric.

26. The female component of claim 1 wherein said backing and the fibers comprising said nonwoven web are comprised of similar materials.

27. The female component of claim 26 wherein said backing and the fibers comprising said nonwoven web are comprised of polyester.

28. The female component of claim 26 wherein said backing and the fibers comprising said nonwoven web are comprised of polypropylene.

29. The female component of claim 1 wherein said nonwoven web is adhesively bonded to said backing.

30. The female component of claim 1 wherein said nonwoven web is autogenously bonded to said backing.

31. The female component of claim 30 wherein said nonwoven web is bonded to said backing by a heat/pressure process.

32. The female component of claim 30 wherein said nonwoven web is bonded to said backing by an ultrasonic process.

33. The female component of claim 1 wherein at least some of the fibers in said nonwoven web are fused to said backing in such a manner that the portions of said fibers adjacent said backing comprise necked-down portions which are thinner than the remaining portions of said fibers so that said necked-down portions of said fibers will be the weakest portion of said fastening device when subjected to the removal of the hooks of said complementary hook fastening component.

34. The female component of claim 1 additionally comprising a layer of 3 denier fibers positioned on the surface of said nonwoven web that faces away from the backing.

35. A female component for a refastenable fastening device, said female component being capable of engaging a complimentary hook fastening component which has a base with individual hooks having blunt heads extending outward from said base, said female component comprising:
a backing, and
a nonwoven fibrous web having a basis weight of between about 18 and about 24 g/m$^2$ so that there is space between the fibers in said fibrous nonwoven web to allow said hook fastening component to penetrate said nonwoven web, said nonwoven web comprised of a plurality of fibers having a denier of between about 0.5 and about 15, wherein the plan view area occupied by any interfiber bonds of said nonwoven web is less than about six percent of the total area of said nonwoven web, said nonwoven web being fused to said backing by bonds in such a manner that the portions of said fibers adjacent said backing comprise necked-down portions which are thinner than the remaining portions of said fibers so that said necked-down portions of said fibers will be the weakest portion of said fastening device when subjected to the removal of the hooks of said complimentary hook fastening component and so that the total plan view bonded area occupied by both any inter-fiber bonds of said nonwoven web and by the bonds between said nonwoven web and said backing is between about 10 percent and about 35 percent of the total area of the female component, said nonwoven web being secured to said backing by bonding means that form bonded areas that are spaced apart less than or equal to a distance of about ½ the length of the fibers in a nonwoven web.

36. The female component of claim 35 wherein the plan view area occupied by any inter-fiber bonds of said nonwoven web is less than about 2½ percent of the total area of said nonwoven web.

37. The female component of claim 35 wherein the total plan view bonded area is between about 10 percent and about 18 percent of the total area of the female component.

38. The female component of claim 35 wherein said bonded areas are continuous and disposed in a pattern.

39. The female component of claim 35 wherein said nonwoven web is carded, and is comprised of randomly oriented fibers that have lengths between about 5 cm. and about 8 cm.

40. The female component of claim 35 wherein said nonwoven web is spunbonded, and is comprised of continuous length fibers primarily oriented in a single direction.

41. The female component of claim 35 wherein fibers in said nonwoven web are crimped with a crimping frequency of at least about 4 crimps/cm.

42. The female component of claim 35 wherein said nonwoven web is resilient.

43. The female component of claim 35 wherein said backing comprises a film.

44. The female component of claim 35 wherein said nonwoven web is bonded to said backing by a heat/pressure process.

45. The female component of claim 35 wherein said nonwoven web is bonded to said backing by an ultrasonic process.

46. The female component of claim 35 additionally comprising a layer of 3 denier fibers positioned on the surface of said nonwoven web that faces away from the backing.

47. The female component of claim 35 wherein said female component has a planar outwardly facing surface.

* * * * *